United States Patent [19]

Lopez

[11] Patent Number: 4,782,841

[45] Date of Patent: Nov. 8, 1988

[54] MEDICAL DEVICE

[75] Inventor: George A. Lopez, Huntington Beach, Calif.

[73] Assignee: ICU Medical, Inc., Mission Viejo, Calif.

[21] Appl. No.: 129,362

[22] Filed: Nov. 30, 1987

Related U.S. Application Data

[63] Continuation of Ser. No. 35,434, Apr. 7, 1987, abandoned, which is a continuation-in-part of Ser. No. 849,148, Apr. 7, 1986, abandoned.

[51] Int. Cl.$^4$ .................................................. A61B 5/00
[52] U.S. Cl. ..................................... 128/164; 604/198; 604/263
[58] Field of Search ............... 604/198, 263, 192, 187; 128/763, 764, 765

[56] References Cited

U.S. PATENT DOCUMENTS

4,573,976 3/1986 Sampson et al. ............... 604/198
4,655,751 4/1987 Harbaugh ....................... 604/198
4,666,435 5/1987 Braginetz ........................ 604/198

Primary Examiner—John D. Yasko
Attorney, Agent, or Firm—Knobbe, Martens, Olson & Bear

[57] ABSTRACT

Disclosed is a vacuum tube type collection device for collecting blood or other body fluids from a patient. The device includes a conventional sealed vacuum tube received in a tube holder having a removable needle assembly connected to the tube holder. The characterizing feature of the device of this invention is that the needle assembly has a guard member which protects the exposed tip of the needle after withdrawal of the needle from the patient's body. This member is movable between a first position where the tip of the needle is exposed and a second position where the guard member covers the tip of the needle and prevents needle sticks. A locking element is mounted along the needle shaft which permanently locks the guard member in the second position upon movement of the guard member into the second position.

13 Claims, 7 Drawing Sheets

MEDICAL DEVICE

RELATED PATENT APPLICATIONS

This application is a continuation of application Ser. No. 35,434, filed Apr. 7, 1987 now abandoned which is a continuation-in-part of Ser. No. 849,148, filed Apr. 7, 1986, now abandoned.

BACKGROUND OF THE INVENTION

1. Field of the Invention

This invention relates to a device for withdrawing blood or other fluids from a patient employing a dual-tip needle element, and particularly relates a device where one of the needle tips is provided with a guard that prevents accidental needle sticks.

2. Background Discussion

It is a common practice in withdrawing from a patient blood samples, or other body fluids, to employ a device which includes a disposable dual-tip needle element. This needle element is removably connected to a reusable tube holder which holds a sealed tube having a partial vacuum in the interior of the tube. Becton Dickinson corporation makes such a sampling device under the brand name of Vacutainer.

The disposable needle element is initially housed within a container that allows the nurse to connect the needle element to the tube holder without directly touching the needle element. This container usually includes a removable cover which surrounds the end (the patient end) of the needle element that will eventually be stuck into the patient's body. The nurse, however, does not remove the cover until she is ready to withdraw blood from the patient, whereupon the patient end of the needle is inserted into the into the patient's body. The other end (the tube end) of the needle element is covered by a cap member which is removed prior to connecting assembly to the tube holder.

With the needle inserted in the patient, the tube is pushed into the tube holder, with the sealed end of the tube being directed towards the tube end of the needle element. As the nurse advances the tube towards the tube end of the needle element, the side walls of the tube holder guide the tube. When the sealed end reaches the tube end of the needle, the needle pierces the sealed end, with the tip of the needle extending into the interior of the tube. The vacuum within the tube causes blood to flow immediately from the patient through the needle element into the interior of the tube, filling it.

Although this device is extremely useful there is one serious problem associated with using it. Namely, accidental needle sticks. Upon removal of the needle from the patient, and in the process of disconnecting the needle element from the tube holder, the nurse recovers the exposed patient end of the needle. When this is done, there is the possibility that an accidental needle stick will occur. When this happens, the nurse is required to undergo a blood test to determine if she is already carrying an infectious disease. If she is not and later becomes infected, the hospital employing the nurse will be legally liable.

SUMMARY OF THE INVENTION

The problem discussed above has been obviated by the present invention which provides a simple, safe, and convenient way to protect the user against accidental needle sticks after withdrawal of the needle element from the body of the patient. There are several features of this invention, no single one of which is solely responsible for its desirable attributes. Without limiting the scope of this invention, as expressed by the claims, its more prominent features will now be discussed briefly. After considering this discussion, and particularly after reading the section of this application entitled DETAILED DESCRIPTION OF THE PREFERRED EMBODIMENTS, one will understand how the features of this invention provide the advantages of simplicity, convenience, and safety.

One feature of the present invention is the use of a guard to cover the needle as it is withdrawn from the body of the patient. This guard is mounted on the shaft of the needle and has associated with it a locking element that permanently locks the guard in position covering the tip of the needle. The guard is adapted to move between a first position exposing the tip of the needle to a second position covering the tip of the needle. The second feature of this invention is that the needle element may be a unitary structure or be formed of separate components. The locking element is securely connected to the shaft of the needle and is designed to permanently lock the guard in the second position upon movement of the guard to the second position.

In one embodiment of this invention, the needle element is a unitary structure with both segments of the needle being embedded in a common connector section. In another embodiment of this invention, the needle element is in two separate sections which are detachably connected together.

The preferred embodiments of this invention illustrating all of its features will now be discussed in detail. These embodiments show the device of this invention being used with a conventional vacuum withdrawal device, with the improvement being directed to the disposable needle element being equipped with a guard member.

BRIEF DESCRIPTION OF THE DRAWING

The device of this invention is illustrated in the drawing, with like numerals indicating like parts, and in FIG. 1 is a perspective view of the device of this invention.

FIG. 2 is a perspective view of the needle assembly of this invention.

FIG. 3 is an exploded enlarged view of the needle assembly shown in FIG. 2.

DESCRIPTION OF THE PREFERRED EMBODIMENTS

Figures 1, 2, 3:
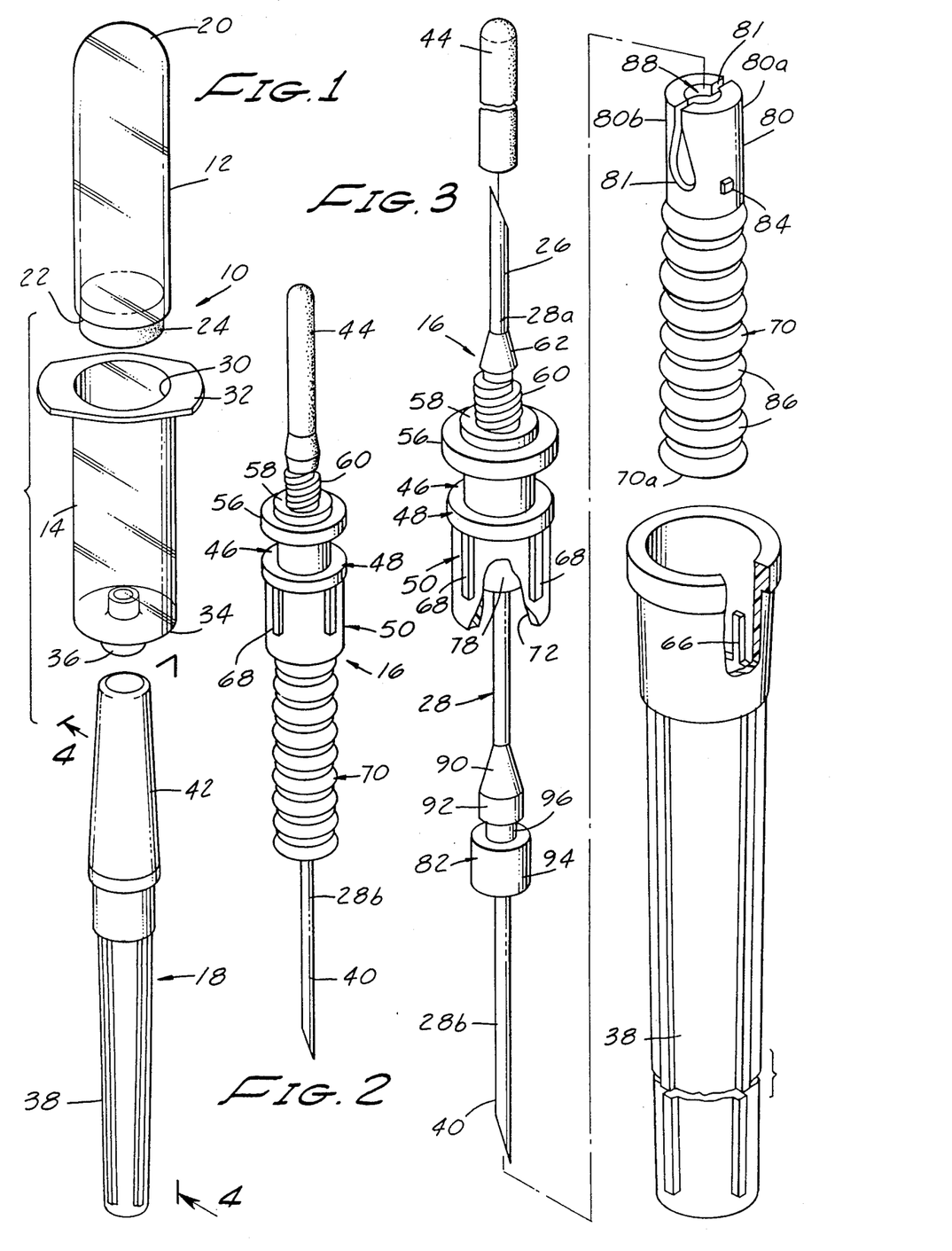

As best shown in FIG. 1, the device 10 of this invention includes three components: a vacuum collection tube 12, a tube holder 14, and a disposable needle assembly 16 (FIG. 2) contained within a housing 18. The collection tube 12 and tube holder 14 are of conventional design. The disposable needle assembly 16 is the unique feature of the device 10.

The vacuum collection tube 12 may be a glass or plastic tube having a closed 20 end and an open end 22 sealed with a self-sealing rubber stopper 24. There is a vacuum on the inside of the tube 12 which causes fluid to be drawn into the interior of the tube when the rubber stopper 24 is punctured. The collection tube 12 is received in the tube holder 14 during use. This tube holder has a generally cylindrical body which guides the collection tube towards the needle end 26 of the needle element 28 (FIG. 3) of the needle assembly 16. The tube holder 14 has an open entry end 30 surrounded by a flange 32 which is gripped by the user during use. Opposite the open entry end is a partially closed port end 34 which has an adapter 36 molded into the partially closed port end. This adapter 36 is designed to removably secure the needle assembly 16 to the tube holder 14. Thus, upon removal of the needle assembly 16 and replacement, the tube holder 14 can be repeatedly used rather than being disposed. Moreover, as frequently is the case, several collection tubes 14 are filled during testing of the same patient prior to replacing the needle assembly 16.

The needle assembly 16 of this invention is best illustrated in FIGS. 2 and 3. This needle assembly 16 is held within the housing 18 which has two portions: a patient needle sheath 38 which covers the patient end 40 of the needle element 28 and a cover 42 which covers the needle end 26 of the needle element 28. The end of the sheath 38 sits within the open mouth of the cover 42, with the combined structure of sheath and cover forming the housing 18 which encases the needle assembly 16. Prior to connecting the needle assembly to the tube holder, the cover 42 is removed to expose the tube end 26 of the needle element. The needle end 26 is covered by a rubber cap 44 which fits snugly over the it. As will be explained in greater detail hereafter, this rubber cap 44 acts as a valve to close off the tip of the needle end 26 upon removal of the tube 12 from the tube holder 14.

The needle assembly 16 includes the needle element 28 which is mounted to a hub 46. One segment 28a of the needle element 28 projects from one side of the hub 46 and the other segment 28b projects from the opposite side of the hub, with the ends 26 and 40 of the needle element being opposed to one another and the longitudinal axis of these segments disposed along the longitudinal axis of the hub.

Figure 5:
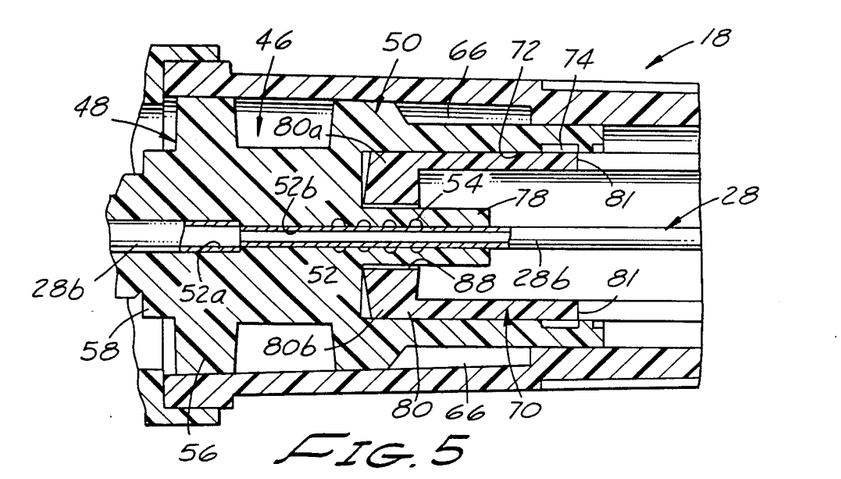
FIG. 5 is a cross-sectional view taken along line 5—5 of FIG. 4.
Figure 6:
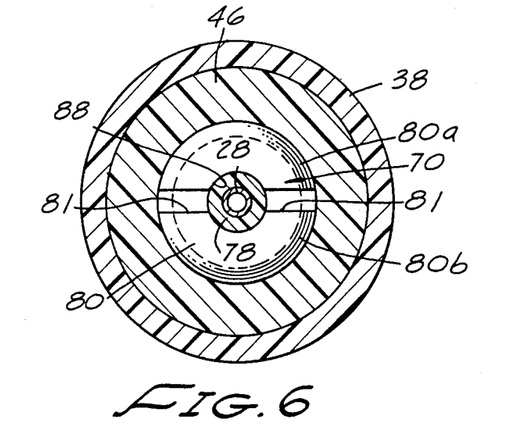
FIG. 6 is a cross-sectional view taken along line 6—6 of FIG. 4.

The hub 46 has a connector section 48 and a sheath carrier section 50. This hub 46, including the sections 48 and 50, is molded from plastic to provide a unitary structure having a central passageway 52 therein which receives the two needle segments 28a and 28b. The segment 28a has a slightly larger diameter than the segment 28b of the needle element 28. As shown in FIG. 5, both of these segments 28a and 28b are lodged within the passageway having two sections 52a and 52b with different diameters. The needle segments 28a and 28b may be molded in place or an adhesive may be used to bond the segments securely to the hub 46. In the later case, there is provided a series of annular recesses 54 about the section 52b of the passageway 52 into which an adhesive is placed to secure the needle segment 28b in position.

Figure 11:
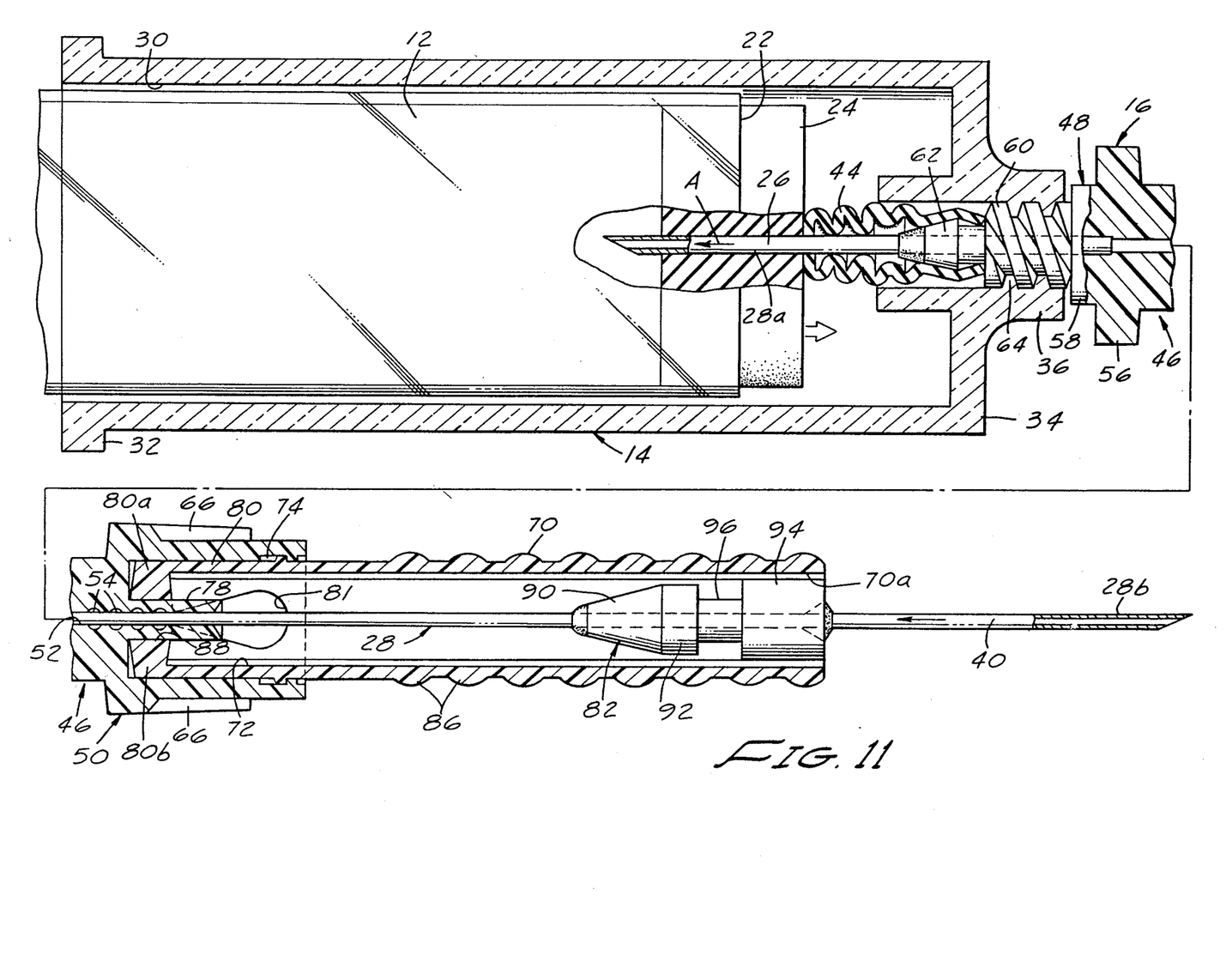
FIG. 11 is a cross-sectional view, with sections broken away, similar to that shown in FIG. 10 with the tube moved inwardly so that the tube end of the needle penetrates the sealed end of the tube.

The connector section 48 of the hub 46 includes a disk portion 56 having a raised cylindrical platform 58 extending from the side of the disk which faces the tube holder 14 upon connection of the needle assembly 16 to the holder. A threaded section 60 extends outwardly from this side of the platform 58 and terminates in a nozzle-like element 62 which fits into the open end of the rubber cap 44. As shown in FIG. 11, to connect the needle assembly 16 to the tube holder 14, the user simply screws the threaded section 60 into the open exterior end of the adapter 36 which has corresponding internal threads 64 to allow the user to simply rotate the needle assembly to secure it to the tube holder.

Figure 7:
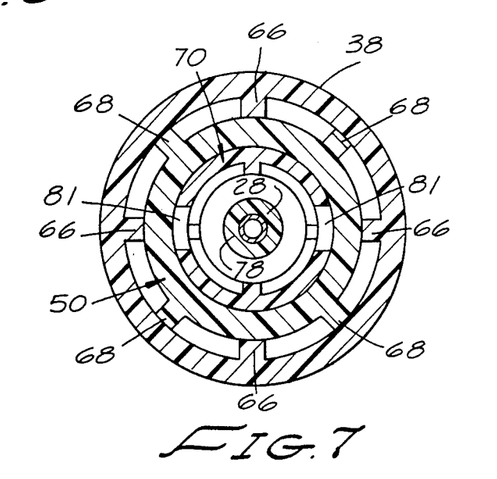
FIG. 7 is a cross-sectional view taken along line 7—7 of FIG. 4.
Figure 8:
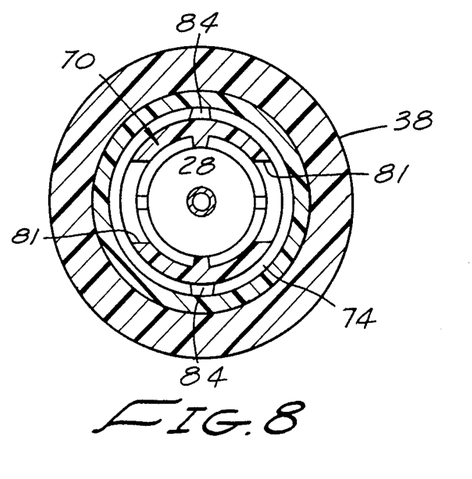
FIG. 8 is a cross-sectional view taken along line 8—8 of FIG. 4.
Figure 9:
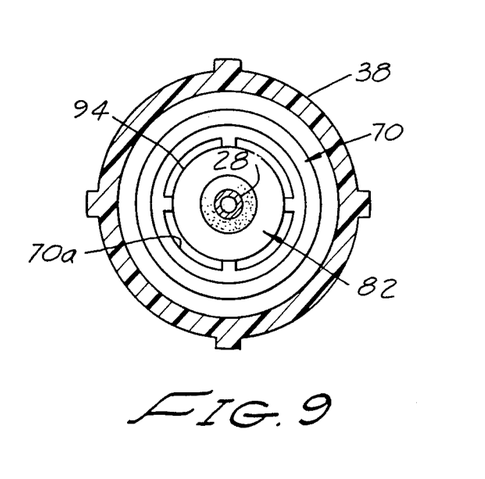
FIG. 9 is a cross-sectional view taken along line 9—9 of FIG. 4.
Figure 10:
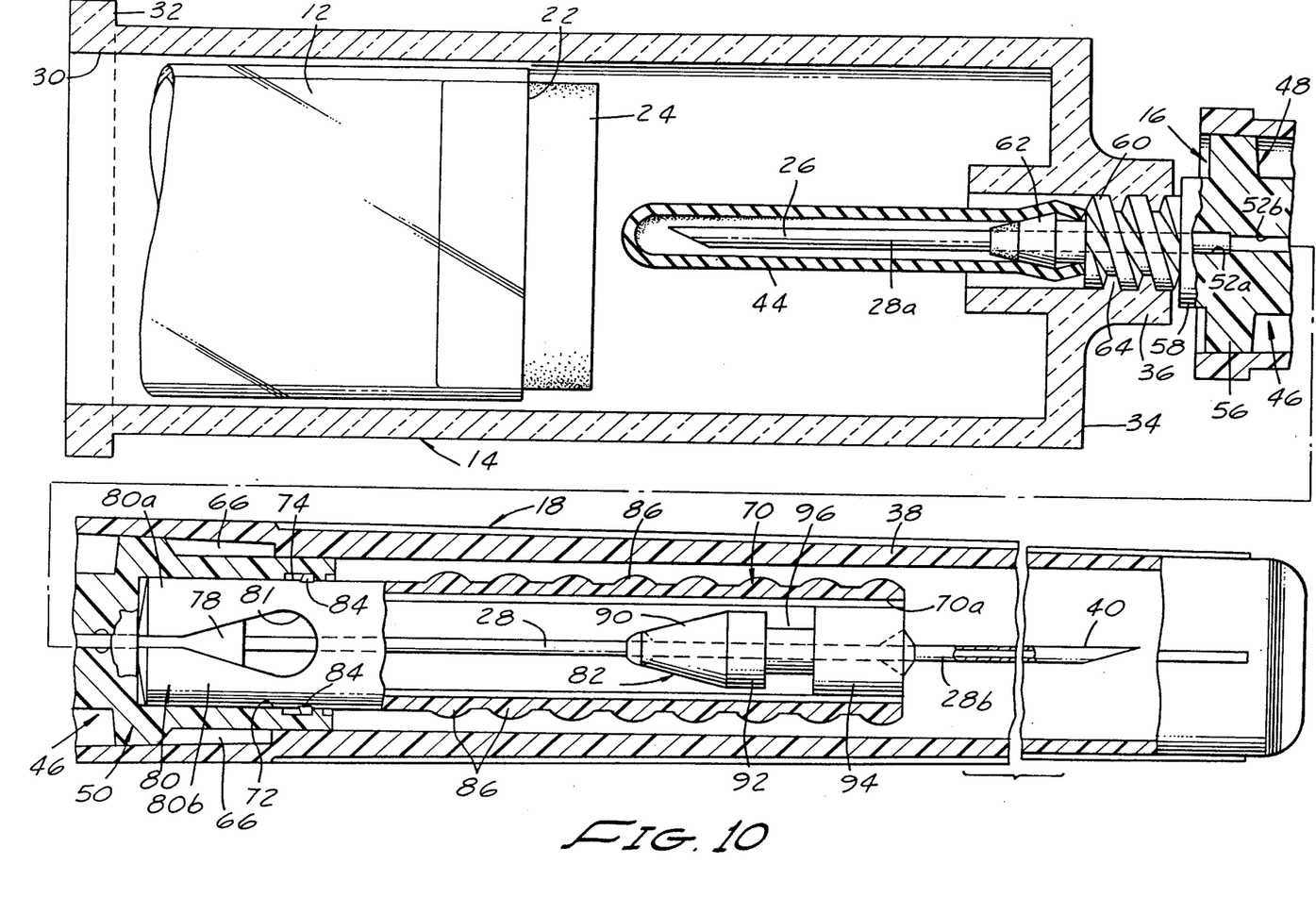
FIG. 10 is an enlarged cross-sectional view, with sections broken away, showing the needle assembly connected to the tube holder and the tube being moved towards the inwardly projecting tube end of the needle element.

As best shown in FIG. 10, the sheath 38 covering the patient end 40 of the needle element 28 is retained in position covering the patient end of the needle element until the needle assembly 16 is connected to the tube holder 14. The sheath 38 includes internal splines 66 (FIG. 3) running lengthwise along the inside wall of the sheath. As illustrated best in FIG. 7, these splines 66 coact with a rib 68 carried on the outside wall of the sheath carrier section 50 of the hub 46. The splines 66 abut the sides of the ribs 68 upon applying a torque to the sheath so that the splines will push against the ribs to turn the needle assembly 16, screwing it into the adapter 36. To disconnect the needle assembly 16 from the tube holder 14, the sheath 38 again is placed in position covering the patient end 40 of the needle element 28 and rotated in an opposite direction to unscrew the connector section 48 from the adapter 36. In this instance, the splines 66 will also coact with the ribs 68 to apply turning force to the needle assembly 16.

Figure 4:
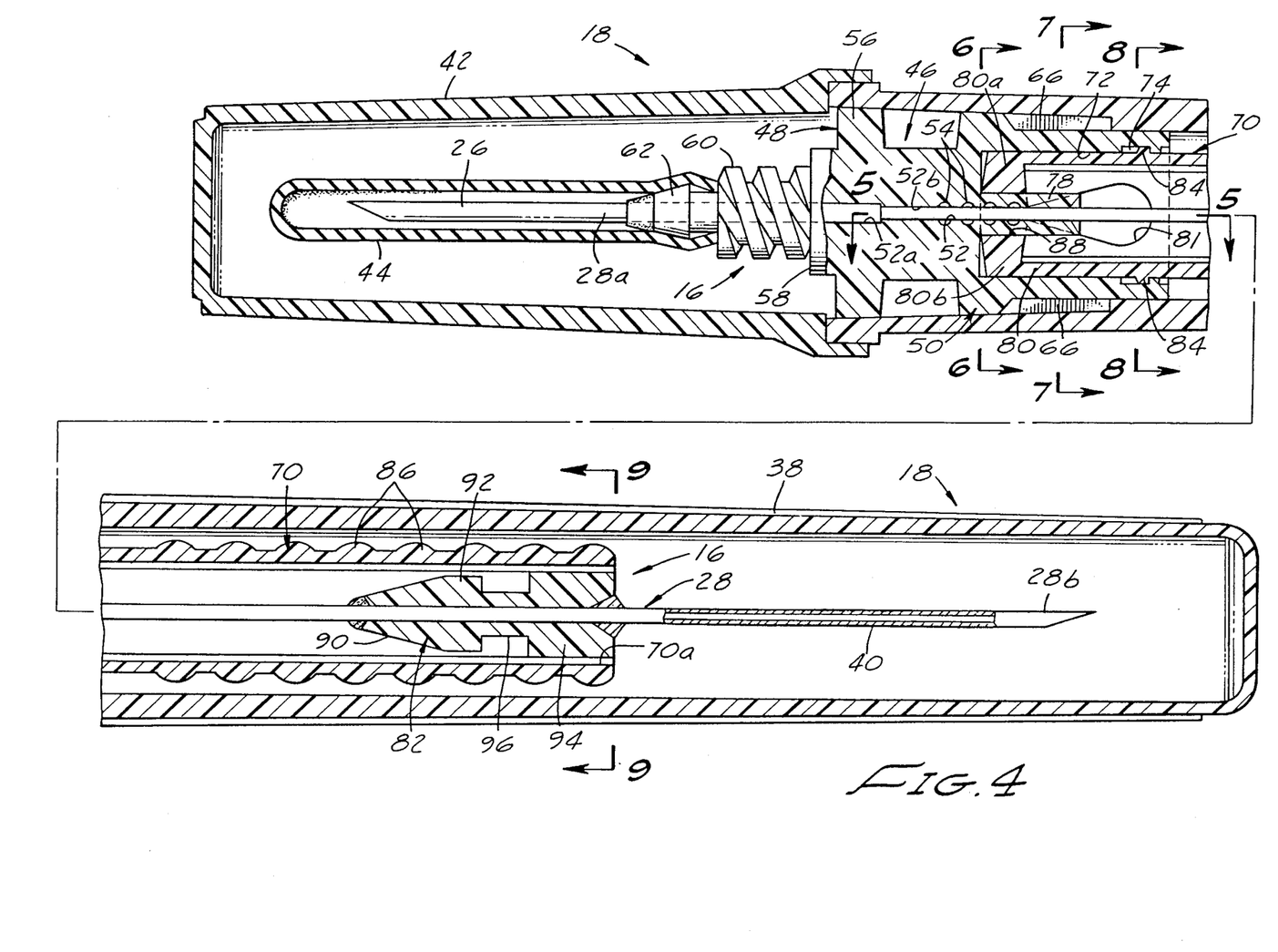
FIG. 4 is a cross-sectional view taken along line 4—4 of FIG. 1.
Figures 12, 13, 14:
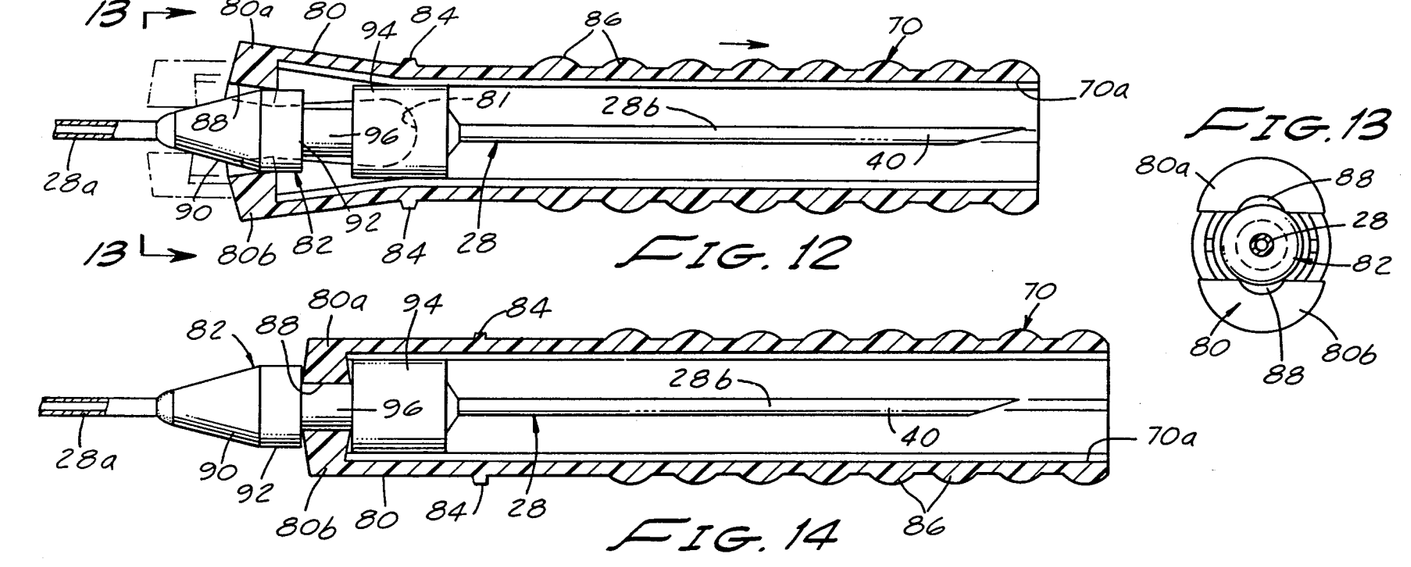
FIG. 12 is a cross-sectional view showing the guard member being moved forward to cover the tip of the needle.
FIG. 13 is a cross-sectional view taken along line 13—13 of FIG. 12.
FIG. 14 is a cross-sectional view similar to that shown in FIG. 12 with the guard member moved completely forward and locked permanently in position to cover the tip of the patient end of the needle element.

The characterizing feature of this invention is a guard 70 which is mounted to move axially along the shaft of the needle element 28 from a rearward position as shown in FIG. 4 to a forward position shown in FIG. 14. In this forward position the guard 70 covers the tip of the patient end 40 of the needle element 28 and protects the user against accidental needle sticks.

The sheath carrier section 50 of the hub 46 is designed to hold the guard 70 in the position illustrated in FIG. 4 until the user is ready to move the guard forward to cover the tip of the patient end 40 of the needle element 28. This sheath carrier section 50 is best illustrated in FIGS. 3, 4 and 5. It is integral with the hub 46 and includes an annular recessed portion 72 which has a circumferential groove 74 at the mouth of the carrier section 50. Extending inwardly into the recessed portion 72 is a neck 78 from which the needle element 28 projects outwardly. In accordance with this embodiment of the invention, the connector section 48 and the sheath carrier section 50 are integral, being molded from the same plastic material to provide a unitary structure.

The guard 70 has a generally cylindrical configuration with the rear section of the guard having a collar 80 which interacts with a locking element 82 secured to the shaft of the needle element 28, and opposite the collar, an open end 70a which has a restricted diameter that prevents the tip of the user's little finger from entering the open end. Thus, when the guard is in the forward position as shown in FIG. 14, the user, even if he or she intentionally pushes his or her little finger into the open end 70a, would not contact the tip of the patient end 40 of the needle element 28. Spaced apart in a row are nipples 84 which project outwardly from the collar 80 and are received in the groove 74 of the sheath carrier section 50 as shown in FIG. 4. Along the exterior of the guard 70 are a series of raised annular gripping elements 86 which assist the user in moving the guard forward along the shaft of the needle element 28. The collar 80 is separated by a pair of opposed lateral tear drop slits 81 in the sidewall of the guard to divide the collar into two generally semi-circular elements 80a and 80b as shown in FIG. 13. Between the ends of these elements 80a and 80b is an open section 88 that interacts with the locking element 82 as illustrated in FIGS. 12, 13 and 14. The semi-circular elements 80a and 80b of the collar 80 each provide a wedge-like piece that grips the locking element 82 as shown in FIG. 14 when the guard 70 is moved forward.

The locking element 82 has a ramp section 90 in the form of a conical member which terminates in a rear shoulder section 92. The forward end of the locking element 82 is in the form of a raised shoulder section 94 with an annular receptacle portion 96 being between the raised shoulders 92 and 94. When the user pushes the guard 70 forward, the elements 80a and 80b of the collar 80 ride up the ramp section 90, with the two collar elements expanding outward. The collar, because of the teardrop slits separating the two sections, has an internal resiliency which allows the elements 80a and 80b of the collar to snap into and wedge themselves in the annular receptacle section 96 as shown in FIG. 14 when the guard 70 is moved to the forward, permanently locking the guard in the forward position.

Operation

To use the device 10, first, the cover 42 for the tube end 26 of the needle element 28 is removed and discarded. Next, the user grips the sheath 38 covering the patient end 40 of the needle element 28 and inserts the connector section 48 of the needle assembly 16 into the adapter 36 of the tube holder 14 turning the needle assembly 16 to screw the threaded section 60 into the adapter. The internal splines 66 of the sheath coact with the ribs 68 on the sheath carrier section 50 to turn the needle assembly as the sheath is rotated by the user.

With the needle assembly 16 connected to the tube holder 14, the sheath 38 is pulled from the assembly to expose the patient end 40 of the needle element 28. The user places the collection tube 12 into the open end 30 of the tube holder 14, grasping the flange 32 with the index finger and middle finger while simultaneously pressing against the end of the tube 20 with the thumb. This pushes the collection tube 20 inwardly towards the tube end 26 of the needle element 28 as illustrated in FIGS. 10 and 11. The tip of the tube end 26 penetrates the stopper 24, and the stopper depresses the rubber cap 44, as the tube 12 advances. As indicated by the arrow A in FIG. 11, blood or other body fluid will flow through the patient end 40 of the needle element 28 into and through the tube end 26 of the needle element into the interior of the collection tube 12. When the tube 12 is filled, the user pulls it from the tube holder, whereupon the rubber cap 44 will return to its normal position as illustrated in FIG. 10. The rubber cap 44 is self-sealing so that the hole produced in it by penetration of the needle element 28 is sealed off, preventing blood from escaping from the tube end 26 of the needle element. Thus, if the user wishes to fill another collection tube, he or she may do so by simply placing another tube in the holder and moving it to the position illustrated in FIG. 11.

Figure 15:
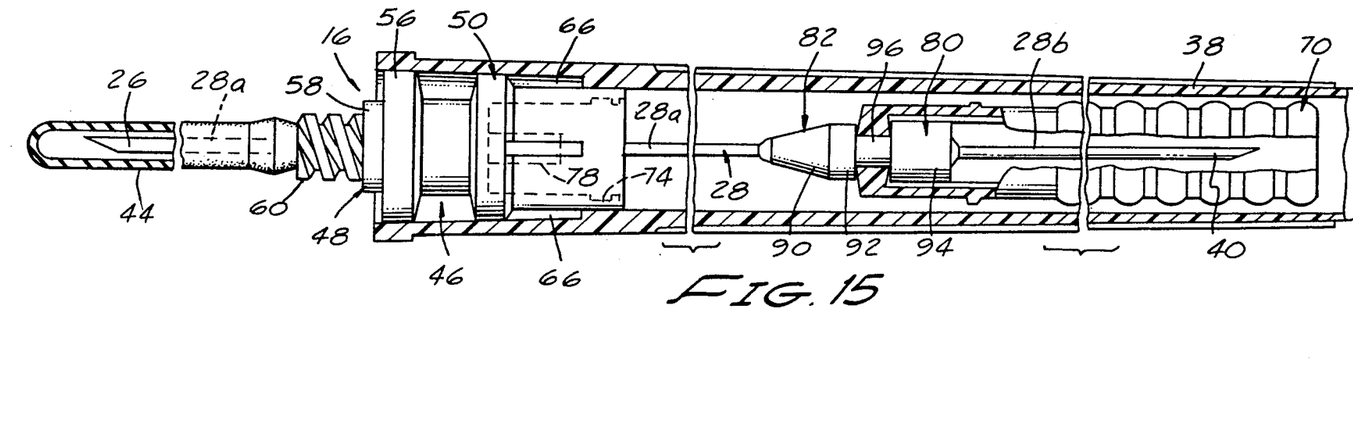
FIG. 15 is a cross-sectional view showing the sheath for the needle assembly recovering the patient end of the needle element, with the needle assembly removed from the tube holder.

When it is time to withdraw the patient end 40 of the needle element 28 from the body of the patient, the user simply grasps the guard 70 by the gripping elements 86 and holds it steady while pulling the tube holder 14 away from the body of the patient. This will cause the guard 70 to move relative to the needle element 28 so that the collar 80 will engage the locking element 82, ride over the ramp section 90 and then snap into position, with the elements 80a and 80b wedging themselves into the annular receptacle 96. This permanently locks the guard 70 in the position shown in FIG. 14. The sheath 38 is then replaced as shown in FIG. 15 and now used to unscrew the needle assembly 16 from the tube holder 14. The needle assembly 16 with the guard in the forward position and the sheath 38 covering the assembly is then discarded.

ALTERNATE EMBODIMENT

Figures 16, 17:
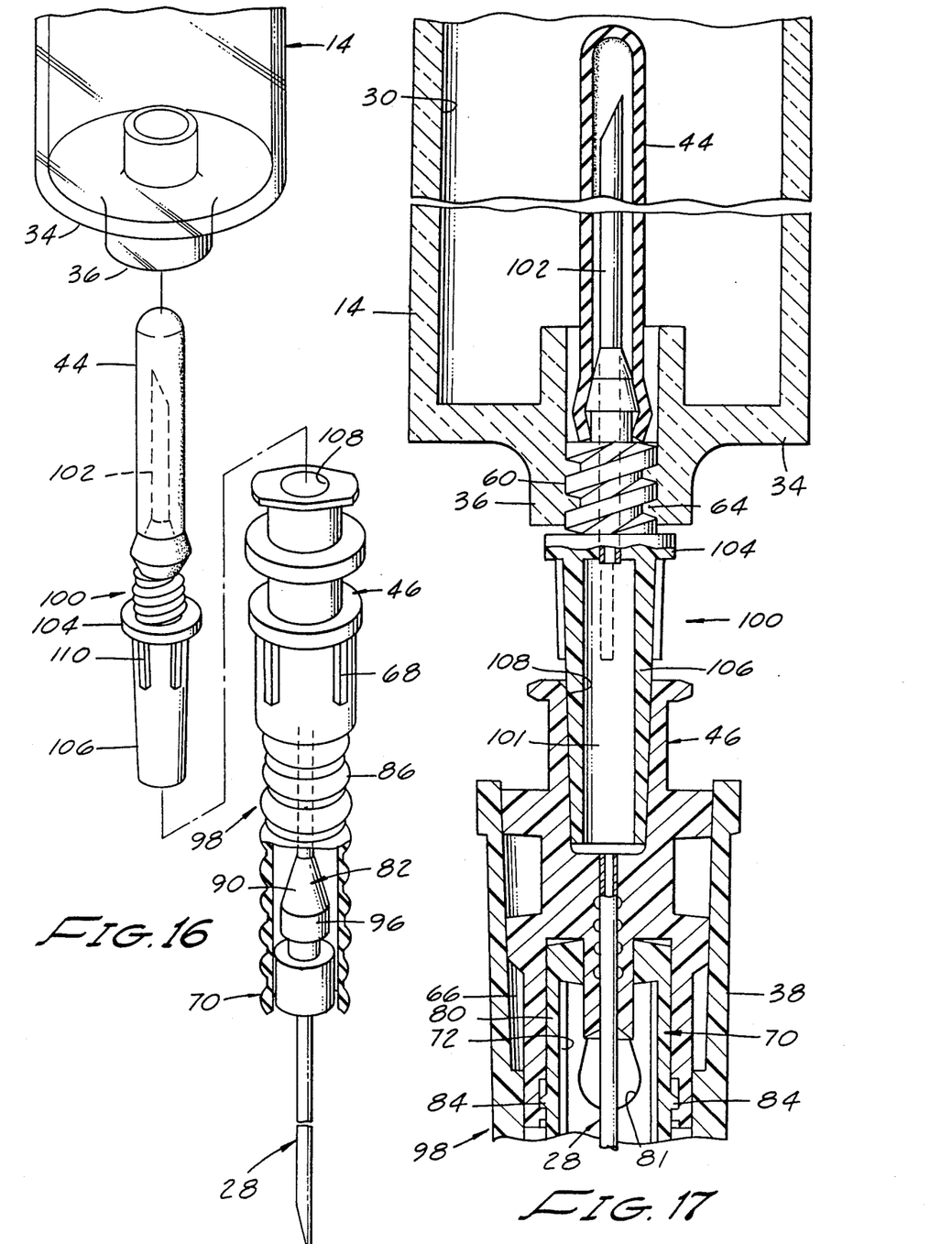
FIG. 16 is an exploded perspective view of an alternate embodiment of the device of this invention.
FIG. 17 is an enlarged cross-sectional view showing the needle assembly illustrated in FIG. 16 connected to the tube holder.

The alternate embodiment of this invention is illustrated in FIGS. 16 and 17. In this embodiment the medical device 98 illustrated in the related parent application, U.S. patent application Ser. No. 06/849,148, is used with a special connector 100. This connector 100 is designed to fit into the open end of the hub 46, thereby allowing the medical device 98 to be used with a vacuum collection tube 12. The connector 100 is designed to include a needle 102 which extends outwardly from molded plastic piece 104 having a tapered section 106 which fits into the open end 108 of the medical device 98. There is an internal passageway 101 in the section 106 that allows fluid to flow from the device 98 through the needle 102.

A cover (not shown) for the connector 100 is used to cover the needle 102 during shipment. This cover has internal splines carried on its side wall which interact with ribs 110 on the exterior wall of the tapered section 106 to permit the cover to be used to screw the connector into the adapter 36. When the connector 100 has been connected to the tube holder 14, as illustrated in FIG. 17, the tapered section 106 is simply force fitted into the open mouth 108 of the medical device 98 allowing this device to be used to collect blood or other fluid from the body of a patient. After being used, the guard 70 is moved forward as discussed previously to cover the patient end 40 of the needle element 28.

SCOPE OF THE INVENTION

The above description presents the best mode contemplated in carrying out the present invention. This invention is, however, susceptible to modifications and alternate constructions from the embodiments shown in the drawing and described above. Consequently, it is not the intention to limit this invention to the particular embodiments disclosed. On the contrary, the intention is to cover all modifications and alternate constructions coming within the spirit and scope of the invention as generally expressed by the following claims.

I claim:

1. In a device used to withdraw blood or other fluids from a patient, including (a) tube means having a seal in an open end adapted to be penetrated by a needle, with said seal then being self-sealing upon withdrawal of the needle penetrating said seal, (b) reusable tube holder means into which the tube means is received during use, said tube holder means having an open end which receives the sealed end of the tube means, (c) opposite the open end, a connector for a needle assembly, and (d) a disposable needle assembly adapted to be removably connected to the tube holder means, the improvement wherein the needle assembly includes needle means having a first needle segment extending into the tube holder means upon connection with the tube holder means and a second needle segment extending outwardly from the tube holder means upon connection of the needle assembly to the tube holder means with the tip of the second needle segment being exposed prior to insertion of this second segment into the patient, a guard member mounted on the shaft of the second needle segment and movable axially along the shaft of said second needle segment between a first position where the guard means is displaced inwardly from the tip to expose said tip to enable it to penetrate the body of a patient and a second position where the guard member covers said tip to prevent needle sticks, and locking means mounted along said needle shaft which permanently locks the guard member in the second position upon movement of said guard member from the first position to the second position.

2. The device of claim 1 wherein the needle assembly is a unitary structure having a body member with said first and second needle segments aligned along a common axis and extending outwardly from the body member.

3. The device of claim 1 wherein the needle assembly has two separate sections which are adapted to be detachably connected together, one of said sections carrying one needle segment and the other section carrying the other needle segment.

4. The device of claim 3 wherein said needle segments are aligned along a common axis upon connecting the two sections together.

5. A disposable needle assembly including an elongated needle element terminating at first and second opposed pointed tips, a connector member mounted between the opposed tips of the needle element for removably connecting the needle assembly to a tube holder of a blood withdrawal device, a guard member mounted on the needle element and movable axially along the needle element between a first position where the guard means is displaced inwardly from the first pointed tip to expose said first tip to enable it to penetrate the body of a patient and a second position where the guard member covers said first tip to prevent needle sticks, and locking means mounted along said needle element between the connector means and said first tip which permanently locks the guard member in the second position upon movement of said guard member from the first position to the second position.

6. The disposable needle assembly of claim 5 wherein the connector member has a threaded element extending therefrom towards the second tip to enable the needle assembly to be screwed into a threaded opening in the tube holder.

7. The disposable needle assembly of claim 6 wherein the connector member has on its exterior rib elements which coact with splines on a needle sheath to facilitate connecting and disconnecting the needle assembly to the tube holder.

8. The disposable needle assembly of claim 5 wherein a rubber cap is seated on the second tip of the needle.

9. A disposable needle assembly including an elongated needle element terminating in first and second opposed pointed tips, a connector member mounted along the needle element between said opposed tips of the needle element for removably connecting the needle assembly to a tube holder of a blood withdrawal device, said connector member having a recessed guard holding section at one end and a threaded tube connection section at the other end, a guard member mounted on the needle element and movable axially along the needle element between a first position where the guard means is displaced inwardly from the first pointed tip to expose said first trip to enable it to penetrate the body of a patient and a second position where the guard member covers said first tip to prevent needle sticks, said guard member in the first position being seated in the recessed guard holding section, and locking means mounted along said needle element between the connector means and said first tip which permanently locks the guard member in the second position upon movement of said guard member from the first position to the second position.

10. The needle assembly of claim 9 wherein the guard member and recessed guard holding section each including interactive elements which hold the guard member in said recessed section until the guard member is manually moved to the second position.

11. A needle assembly including an elongated needle element terminating at one end in a pointed tip, a connector member displaced inwardly from said pointed tip mounted on the needle element for removably connecting the needle assembly to a tube holder, a guard member mounted on the needle element and movable axially along the needle element between a first position where the guard member is displaced inwardly from the tip to expose said tip to enable it to penetrate the body of a patient and a second position where the guard member covers said tip to prevent needle sticks, and locking means mounted along said needle element between the connector means and said first tip which permanently locks the guard member in the second position upon movement of said guard member from the first position to the second position.

12. The needle assembly of claim 11 wherein the connector member has a tapered open end which receives a needle carried in a hollow tapered fitting.

13. A medical device comprising
- a tube holding member which removable receives a vacuum tube having a sealed end,
- a needle element having a first end extending into the tube holding member and adapted to penetrate the sealed end of the vacuum tube upon insertion of the tube into the tube holding member and a second end extending outwardly from the tube holding member and adapted to penetrate the body of a patient,
- a guard member mounted to be moved between a retracted position exposing the second end of the needle and an extended position covering the second end of the needle, and
- locking means for permanently locking the guard member in the extended position upon movement to said extended position.

* * * * *